United States Patent
Murray

(10) Patent No.: US 10,829,398 B2
(45) Date of Patent: Nov. 10, 2020

(54) PHOTOBIOREACTOR

(71) Applicant: INDUSTRIAL PHYCOLOGY LIMITED, Bath (GB)

(72) Inventor: Daniel Murray, Bath (GB)

(73) Assignee: INDUSTRIAL PHYCOLOGY LIMITED, Bath (GB)

( * ) Notice: Subject to any disclaimer, the term of this patent is extended or adjusted under 35 U.S.C. 154(b) by 91 days.

(21) Appl. No.: 14/655,187

(22) PCT Filed: Dec. 5, 2013

(86) PCT No.: PCT/GB2013/053216
§ 371 (c)(1),
(2) Date: Jun. 24, 2015

(87) PCT Pub. No.: WO2014/108665
PCT Pub. Date: Jul. 17, 2014

(65) Prior Publication Data
US 2015/0329395 A1   Nov. 19, 2015

(30) Foreign Application Priority Data

Jan. 9, 2013   (GB) .................................. 1300323.1

(51) Int. Cl.
*C02F 3/28* (2006.01)
*C02F 3/32* (2006.01)
(Continued)

(52) U.S. Cl.
CPC ............... *C02F 3/28* (2013.01); *C02F 3/322* (2013.01); *C12M 21/02* (2013.01); *C12M 21/04* (2013.01);
(Continued)

(58) Field of Classification Search
CPC combination set(s) only.
See application file for complete search history.

(56) References Cited

U.S. PATENT DOCUMENTS

2005/0260553 A1*  11/2005  Berzin .................. B01D 53/85
                                                                 435/3
2008/0178739 A1*   7/2008  Lewnard ............... B01D 53/84
                                                                 95/186
(Continued)

FOREIGN PATENT DOCUMENTS

CN   101405388 A   4/2009
GB     2484530 A   4/2012
(Continued)

OTHER PUBLICATIONS

Matthijs et al. "Application of Light-Emitting Diodes in Bioreactors: Flashing Light Effects and Energy Economy in Algal Culture". Biotechnology and Bioengineering, vol. 50, 1996. p. 98-107 (Year: 1996).*

(Continued)

*Primary Examiner* — Ryan B Huang
(74) *Attorney, Agent, or Firm* — Mossman Kumar & Tyler PC

(57) ABSTRACT

The present invention relates to a photobioreactor for treatment of the waste water. The photobioreactor comprises a treatment chamber for receiving a culture of algae, a water inlet for supplying waste water to said chamber, at least one light source provided within said chamber for providing light to said culture and at least one water outlet for removal of treated water. The at least one water outlet is further arranged in use to selectively remove a proportion of the biomass produced within said chamber when said biomass reaches a predetermined maximum level so as to maintain a continuous or substantially continuous culture of algae within said chamber.

10 Claims, 2 Drawing Sheets

(51) Int. Cl.
*C12M 1/00* (2006.01)
*C12M 1/107* (2006.01)
*C02F 101/10* (2006.01)
*C02F 3/12* (2006.01)
*C02F 11/04* (2006.01)

(52) U.S. Cl.
CPC ............ *C12M 29/18* (2013.01); *C12M 31/10* (2013.01); *C02F 3/1268* (2013.01); *C02F 11/04* (2013.01); *C02F 2101/105* (2013.01); *C02F 2201/3222* (2013.01); *C02F 2203/00* (2013.01); *Y02E 50/30* (2013.01); *Y02W 10/10* (2015.05); *Y02W 10/37* (2015.05)

(56) References Cited

U.S. PATENT DOCUMENTS

| | | | |
|---|---|---|---|
| 2010/0227389 A1 | 9/2010 | Shvabsky et al. | |
| 2010/0255569 A1* | 10/2010 | Camarate de Albuquerque Maranhao | C12M 21/02 435/292.1 |
| 2011/0107664 A1* | 5/2011 | Rancis | A01G 33/00 47/1.4 |
| 2011/0247977 A1* | 10/2011 | Song | A01H 4/001 210/602 |
| 2011/0266215 A1* | 11/2011 | Robinson | C02F 1/30 210/602 |
| 2013/0175301 A1 | 7/2013 | Ray | |

FOREIGN PATENT DOCUMENTS

WO 2007/076187 A2 7/2007
WO WO 2010115996 A1 * 10/2010 ............ C12M 21/02

OTHER PUBLICATIONS

Int'l Examination Report in GB Appln. 1300323.1 dated Jul. 5, 2013.
Int'l Examination Report in GB Appln. 1300323.1 dated Mar. 24, 2014.
Int'l Examination Report in CN Appl. 201380069874.6 dated May 4, 2016.

* cited by examiner

PHOTOBIOREACTOR

FIELD OF THE INVENTION

The present invention relates to a photobioreactor, a system and a method for algal based waste water treatment.

BACKGROUND OF THE INVENTION

The control of phosphate levels in treated waste water is an important challenge for the wastewater industry. Current methods for reducing the phosphate level of wastewater to an acceptable level typically comprise the use of flocculants, such as for example ferric sulphate. These methods are expensive, yield toxic waste and require careful process optimisation to prevent effluent regulation for ferric compounds and phosphate being exceeded. These methods may also result in inefficient removal of phosphates and/or escape of ferric compounds into river courses which may lead to environmental damage.

It has been discovered that algae can be used to significantly reduce the phosphate content in waste water. The algae are generally exposed to the waste water within a photobioreactor. Conventional methods and systems for using algae to treat waste water have a number of drawbacks including requiring a large amount of space, contamination problems, energy requirement, vulnerability to the weather, and unsuitability for industrial scale use. For example, the conventional systems typically make use of sunlight and outdoor culturing. These systems are therefore limited to regions with optimal conditions and as a result have reduced efficiency and limit the scope for using these systems to treat waste water with algae on an industrial scale.

There is therefore a need for an improved photobioreactor which addresses one or more of the problems associated with conventional systems for treating waste water. In particular, there is a need for an improved photobioreactor which can be used on an industrial scale to treat wastewater with improved efficiency.

SUMMARY OF THE INVENTION

According to a first aspect, the present invention provides a photobioreactor for the treatment of waste water comprising:
   a treatment chamber for receiving a culture of algae;
   a water inlet for supplying waste water to said chamber;
   at least one light source provided within said chamber for providing light to said culture; and
   at least one water outlet for removal of treated water; wherein
   the at least one water outlet is further arranged in use to selectively remove a proportion of the biomass produced within said chamber when said biomass reaches a predetermined maximum level so as to maintain a continuous or substantially continuous culture of algae within said chamber.

According to a second aspect, the present invention provides a method of treating waste water comprising contacting a culture of algae with a waste water input in a photobioreactor or system as described herein to produce an algal biomass and a treated waste water output.

Embodiments of the present invention therefore, advantageously, provide an efficient, highly productive, all climate, internally lit, continuous or substantially continuous photobioreactor and the use thereof to treat waste water. The photobioreactor is preferably fully isolated from contaminating environments.

The term "continuous or substantially continuous culture" is used herein to refer to a culture which is present within the chamber of the photobioreactor throughout the treatment process while simultaneously allowing the harvesting of a proportion of biomass when the biomass within the chamber reaches a predetermined maximum level. No additional culture is required to be added to the chamber. The continuous or substantially continuous culture is present within the chamber at a concentration of at least a predetermined minimum level. The removal of the biomass causes dilution of the culture within the chamber during the treatment process. The dilution of the culture is controlled so that the concentration of the continuous or substantially continuous culture within the chamber does not fall below the predetermined minimum value.

The photobioreactor may be arranged such that the retention time of the biomass within the chamber is independent from the retention time of the water within the chamber. By separating the hydraulic retention time from the biomass retention time, treated water can be continuously flowed through the photobioreactor from the inlet to the outlet allowing constant fresh addition of waste water and advantageously boosting the maximum biomass capacity. The photobioreactor therefore enables a significant increase of waste water to be treated by a given volume of culture of algae. The biomass may be harvested when the biomass reaches a predetermined maximum limit.

The chamber may have any suitable shape, for example the chamber may be substantially cylindrical in shape. The outlet may comprise a first outlet arranged in use for allowing the continuous flow of treated water from the chamber and a second outlet arranged in use to selectively remove a proportion of the biomass. The biomass may be removed with the treated waste water. The arrangement of the first and second outlets may be such that the distance between the first outlet and the base of the chamber may be greater than the distance between the second outlet and the base of the chamber. The first and second outlets may be aligned along a direction extending substantially parallel to the longitudinal axis of the chamber.

The photobioreactor could be installed towards the end of existing waste water treatment systems. For example, the photobioreactor may be used as a final polishing stage at the end of existing waste water treatment systems.

Maintaining a continuous or substantially continuous culture has the benefit that the biomass produced can be regularly harvested while still maintaining a high density active culture within the photobioreactor. The photobioreactor of the present invention may offer the potential to save space compared to conventional systems. Advantageously, the photobioreactor and method of the invention may provide a high rate of throughput of water treatment while still providing the harvesting of biomass. The biomass may be harvested at a rate comparable to growing and harvesting a single batch in a non-continuous conventional system. The harvested biomass may then be introduced into an anaerobic digester, for example for gas production.

The method may further comprise determining the biomass increase/growth rate and comparing to a predetermined biomass/cell count, for example an ideal biomass/cell count, and regularly diluting the culture accordingly. The culture may be diluted every 24 hours in order to maintain the biomass at this predetermined level. The culture may be diluted by for example 20% every 24 hours.

The at least one light source may be calibrated to emit light predominantly at wavelengths which enhance photosynthesis. The at least one light source may therefore be calibrated to enable more efficient growth rate of the culture. Chlorophyll is most efficient at absorbing red light. Light from other wavelengths is only partially absorbed. The at least one light source is preferably calibrated to provide light having predominantly a wavelength in the region of 620 to 645 nm, for example to provide red light. The light source may emit light having a greater proportion of red light than blue light. By calibrating the wavelength of the light source the method and photobioreactor of the invention provide for improved efficiency and energy cost savings as energy is not wasted on wavelengths which are not used by the culture of lost as heat.

The at least one light source may comprise at least one light emitting diode (LED). LEDs have the vast potential for power savings making artificial illumination of photobioreactors cost effective.

The photobioreactor may comprise at least one light source in the form of an elongate column. For example, the at least one LED may be in the form of an elongate column. The elongate column may be arranged to extend within the chamber in a direction extending substantially parallel to the longitudinal axis of the chamber. For example, the elongate column may be arranged to extend in a direction extending substantially perpendicular to the base of the chamber. The at least one elongate columns may be spaced apart from each other so as to provide uniform light coverage, for example uniform light intensity within the chamber.

The light source(s) may be programmable. For example, the LED(s) may be high frequency flashing light(s) (FLE). The high frequency flashing light(s) may be adjusted to control the amount of light that impinges the culture.

The photosynthetic reaction taking place in chlorophyll in the culture proceeds at a maximum energetic efficiency. The reaction can be split into two sections; the light and dark dependent reaction centres. Initially the light dependent reaction in chlorophyll captures the energy from incoming light in the light receiving centre. Through a number of chemical reactions the initial energy is passed to a dark reaction centre for use in further photosynthetic reactions. The light dependent reaction centre can only absorb a set amount of energy per second before the reaction centre becomes saturated. If excess light is rendered into the light reaction centre e.g. by continuous lighting, this energy is wasted. This wasted energy has the potential to lead to photo bleaching which may reduce the efficiency of the photosynthesis. Photo bleaching may also cause permanent damage to the cell.

The use of high frequency flashing lights advantageously allows the emission of light to be controlled such that the light energy is only provided when the light dependent reaction of photosynthesis is receptive to the energy. Accordingly, the use of high frequency flashing lights helps to prevent over saturation of the light reaction centre and as such helps to increase the productivity of the cells photosynthesis reactions.

The use of high frequency flashing lights has advantageously been found to help to produce significant increases in culture population and density. As such, the photobioreactor and method of embodiments of the present invention can be used to treat waste water with improved efficiency compared to conventional systems.

The flashing rate of the high frequency flashing lights is preferably arranged in use to flash so that the ratio of the period of time in which light is emitted to the period of time in which light is not emitted is approximately 1:2. The high frequency flashing lights may be arranged in use to flash at a rate to emit 10 microseconds of light for every 20 microseconds of dark. The use of high frequency flashing lights also has the further advantage of providing a significant energy saving compared to a non-flashing light source.

Furthermore, cells of the culture can be damaged by the use of light having an intensity greater than a threshold intensity. However, it has advantageously been found that the photobioreactor can use high frequency flashing lights to emit light with an intensity above the threshold intensity without causing damage to the culture. The applicant has found that when using high frequency flashing lights this increased light intensity of the light pulse is not provided long enough to damage the photosynthetic mechanisms within the cells.

The photobioreactor may therefore enable light from the light source to penetrate to a greater extent, for example to a greater depth within the culture than conventional systems due to the provision of a flashing light source emitting light pulses having increased intensity, for example an intensity greater than the threshold intensity. The increased penetration distance within the culture increases the photoactive layer of the culture. The depth of the photoactive layer is one of the major limitations of conventional photobioreactors. Conventional bioreactors, having continuous illumination, are designed with small capacities in order to reduce light energy waste resulting from the photoactive layer being short.

The light source may be a variable intensity light source. Accordingly, in use the light intensity of the light source may be variable. The method may further comprise adjusting the light intensity of the light source during the wastewater treatment process. The light intensity may be varied in response to the increasing density of the culture. For example, as the treatment process progresses and the culture density increases within the photobioreactor, the light intensity may be increased. The light intensity of the light source may be directly dependent on the density of the culture. The light intensity of the light source may be increased as a function of time as the treatment process continues. The light intensity may be increased over a predetermined period of time. The light intensity of the light source may be controlled or varied so as to provide the required level of lighting to the culture for each stage of the process.

The photobioreactor may further comprise an insulating layer. The insulating layer may be arranged in use to regulate/control the heat within the chamber. The waste water inlet and/or outlet(s) may each comprise a valve.

The photobioreactor may further comprise at least one membrane. For example, the photobioreactor may comprise a membrane arranged in use to ensure the sterility of the culture is maintained. The first membrane may be positioned adjacent to or at the waste water inlet into the treatment chamber.

The photobioreactor may comprise a membrane arranged in use to retain the culture within the treatment chamber while allowing the treated waste water to pass through the outlet. The pore size of the membrane is preferably selected to retain the biomass within said chamber. For example, a membrane may be located adjacent to or at the treated water and biomass outlet. The membrane may be moveable between an open position allowing the biomass/treated water to flow through said outlet and a closed position in which the biomass is retained within the chamber and treated water flows through the outlet. The membrane may be arranged in use to be moved to the open position when the biomass within the chamber reaches the predetermined maximum level.

The at least one outlet of the chamber may comprise a first outlet for removal of treated waste water and a second outlet arranged in use for selectively removing a proportion of biomass. A membrane may be arranged within the chamber so as to be located between said first and second outlet. The membrane may be arranged so as to be located between the waste water inlet and the first outlet. The membrane is preferably arranged in use to retain the biomass within the chamber while allowing treated waste water to be removed by the first outlet. The membrane may be arranged within the treatment chamber to extend at an angle, for example substantially perpendicular, to the longitudinal axis of the chamber at a predetermined height above the base of the chamber. The entire periphery of the membrane is preferably in contact with the chamber walls. The membrane is preferably located within the chamber below the first outlet, for example closer to the base of the chamber than the first outlet. The second outlet is preferably arranged closer to the base of the chamber than the membrane. In this arrangement, the membrane prevents the biomass from being removed from the chamber by the first outlet. The pore size of the membrane is preferably selected to retain the biomass within said chamber.

The chamber may further comprise a gas diffuser. The gas diffuser may be arranged to extend across the full base of the chamber. The gas diffuser is preferably arranged to prevent dead zones and to provide scrubbing to the sides of the chamber and/or the internal light source. The air within the chamber flows upwardly from said base of the chamber. The chamber may further comprise a carbon dioxide nanodiffuser.

The method of the present invention results in an algal biomass being formed during the treatment of waste water. The energy bound within the whole cellular material of the algal biomass may economically be recovered by anaerobic digestion using bacteria. The method may therefore further comprise contacting said biomass with at least one bacterial strain for anaerobic digestion of said biomass. The biomass is preferably contacted with at least one bacterial strain for anaerobic digestion within at least one anaerobic digester. The anaerobic digestion may be performed downstream of said photobioreactor.

In a further aspect, the present invention provides a waste water system comprising at least one photobioreactor as described herein and at least one anaerobic digester for receiving the biomass from the photobioreactor(s) and at least one bacterial strain adapted for digestion of algae. The anaerobic digester is preferably adapted for digestion of algae. The at least one anaerobic digester is preferably located downstream of the photobioreactor(s). The system may comprise the photobioreactor and the digester as an integral unit.

By using the digestion process, the whole of the biomass may be utilised for gas production, such as for example methane gas for power and carbon dioxide. The carbon dioxide may be separated and used, for example recycled as a feed for the algae within the chamber. Advantageously, the liquid and solid fractions leftover are not contaminated by chemical additives. The liquid and solid fractions may be used as liquid or solid fertiliser and/or conditioner. The remaining fractions may include sequestered carbon and clean water. No further chemical processing is required and digestion of the algal biomass advantageously does not produce any toxic waste.

The algal strain for use with the photobioreactor, the method and the system of the invention may be selected from *Chlorella vulgaris*, *Spirulina maxima*, *chlorella-scenesmus*, and *Chlamydomonas reinhardtii*, or a mixture thereof.

The photobioreactor may further comprise a further inlet for supplying metals, such as for example gold and rare earths, to the treatment chamber. The metals may be provided in the form of a slurry. The method may therefore further comprise the step of introducing metals to the treatment chamber of the photobioreactor. The culture ingests the metal and precipitates nanoparticles of the metal within the cell. Nanoparticles of metals are important in modern science and electronics manufacturing. Once the treated waste water and biomass (containing the ingested nanoparticles of metal) pass into the digester, digestion of the algae results in the break up of the biomass and as such provides an easy method for liberating nanoparticles. The method may further comprise the step of recovering the nanoparticles of metals during anaerobic digestion of the biomass, for example in the digester. The metals may be magnetic. The method may comprise use of magnetism to recover nanoparticles of ingested magnetic metals. Embodiments of the photobioreactor and method of the invention may be used to treat waste water and to produce nanoparticles of metals simultaneously.

It has been found that algae may grow within the photobioreactor at a significant rate and as such the culture may be diluted by in excess of 20% a day. By combining several continuous or substantially continuous photobioreactors, it has been found that the combination may produce biomass in excess of the amount of culture used within one photobioreactor within a day for digestion while still maintaining the maximum biomass within the photobioreactor(s). The system may comprise an anaerobic digester for receiving biomass from a plurality of photobioreactor(s).

The system may further comprise a separator arranged in use to separate the treated water from the treated water and biomass obtained from the outlet of the photobioreactor, for example the separator is preferably located between the photobioreactor and the digester.

The use of algae to treat waste water may provide potential for significant gas production, water treatment and profit. Advantageously, the photobioreactor and method of the invention eliminate the limitation of most renewable power, i.e. the variable supply of wind, sun or other environmental parameter The biogas produced by the anaerobic digestion of the biomass within the anaerobic digester(s) may be collected. The biogas is preferably methane. The anaerobic digester(s) may be arranged in use to produce methane at a rate of at least 0.25 L $CH_4$ g $VS^{-1}$, preferably at least 0.5 L $CH_4$ g $VS^{-1}$. The photobioreactor, system and method of the invention may be used to generate power, for example electricity.

In a further aspect, there is provided a method for generating electricity comprising using the biogas generated by the method as herein described and converting said biogas to electricity using a power generator.

In a further aspect, there is provided biomass produced by the method as described herein. The biomass produced by the method of the invention may be used as soil fertiliser or soil conditioner.

In a still further aspect, there is provided treated waste water produced by the method as described herein. The treated waste water advantageously has a lower phosphate content than the waste water input. Preferably, the method of the invention reduces the phosphate levels by at least 75%;

more preferably at least 80%; in particular at least 85%, especially at least 90% compared to the waste water input.

In a further aspect, the present invention provides a kit for waste water treatment comprising at least one photobioreactor or system as herein described and at least one culture of algae. The kit may further comprise at least one anaerobic digester. The kit may further comprise at least one bacterial strain for anaerobic digestion of the biomass.

Whilst the invention has been described above, it extends to any inventive combination of features set out above or in the following description. Although illustrative embodiments of the invention are described in detail herein with reference to the accompanying drawings, it is to be understood that the invention is not limited to these precise embodiments. As such, many modifications and variations will be apparent to practitioners skilled in the art.

Furthermore, it is contemplated that a particular feature described either individually or as part of an embodiment can be combined with other individually described features, or parts of other embodiments, even if the other features and embodiments make no mention of the particular feature. Thus, the invention extends to such specific combinations not already described.

BRIEF DESCRIPTION OF THE DRAWINGS

The invention may be performed in various ways, and, by way of example only, embodiments thereof will now be described, reference being made to the accompanying drawings in which.

Figure 1:
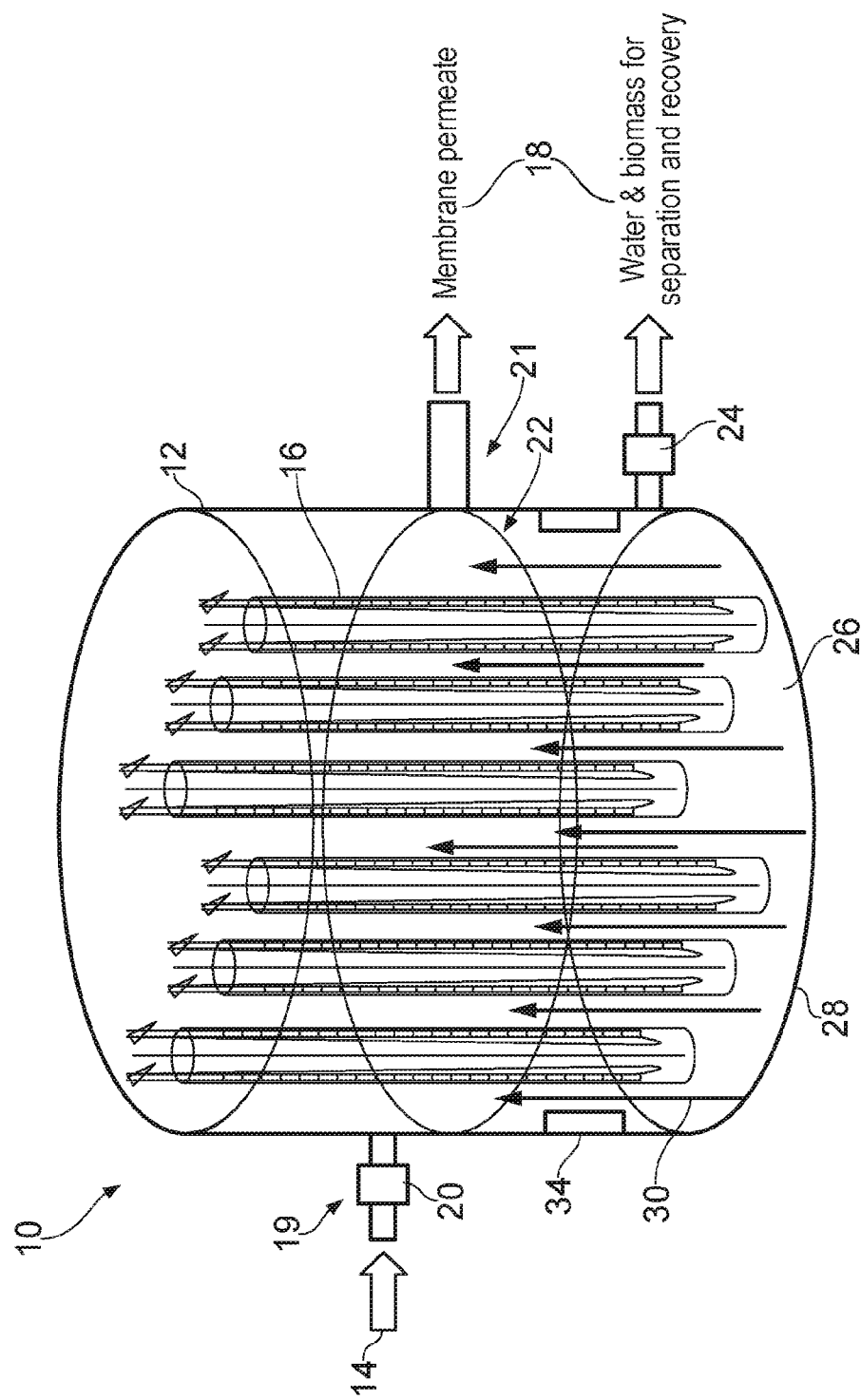
FIG. 1 is a schematic illustration of a photobioreactor according to one embodiment of the invention.

According to FIG. 1, the photobioreactor 10 comprises a cylindrical treatment chamber 12 comprising a waste water inlet 14, six internal LEDs 16 and a treated water outlet 18. The chamber 12 is substantially cylindrical in shape. The LEDs 16 are elongate columns. The LEDs 16 extend substantially parallel to the longitudinal axis of the chamber 12. The LEDs 16 are spaced apart from each other within the chamber to provide uniform light intensity within the chamber 12.

The waste water inlet 14 further comprises a valve 19 and a first membrane 20 arranged in use to maintain the sterility. The treated water outlet 18 comprises a first outlet 21 for maintaining a continuous flow through of treated water. The chamber 12 also comprises a second membrane 22 extending substantially perpendicular to the longitudinal axis of the chamber 12. The second membrane 22 is located closer to the base of the chamber 12 than the first outlet 21. The second membrane 22 is located at a height between the inlet 14 and the first outlet 21. The entire periphery of the second membrane 22 is in contact with the walls of the chamber 12. The second membrane 22 is selected so as to prevent biomass from flowing through the first outlet 21.

The chamber comprises a second outlet 24 arranged in use to selectively remove a proportion of the biomass produced within said chamber 12 when said biomass reaches a predetermined maximum level so as to maintain a continuous or substantially continuous culture of algae within said chamber 12. The first outlet 21 is located at a predetermined distance above the second outlet 24. The second outlet 24 is located closer to the base of the chamber 12 than the second membrane 22.

The chamber 12 further comprises a gas diffuser 26 at the base 28 of the chamber 12. The diffuser 26 is arranged to extend across the full base 28 of the chamber 12. The diffuser 26 is arranged to prevent deadzones within the chamber 12 and to provide scrubbing to the sides of the chamber 12 and/or the internal light source. The air 30 within the chamber 12 flows upwardly from said base 28. The chamber 12 further comprises two carbon dioxide nanodiffusers 34 locating on opposing surfaces of the chamber 12.

In use, a culture of algae (not shown) is placed within the chamber 12. The culture (not shown) is placed towards the base of the chamber 12 and at a location below the height of the second membrane 22. Waste water enters the chamber 12 through the inlet 14. Air is introduced through the base 28. The waste water is contacted with the culture. The LEDs provide light to the culture. The LEDs are arranged to provide a ratio of red:blue light of 3:1. The LEDs are also arranged to be high frequency flashing lights and the light intensity of the LEDs is arranged in use to increase as the biomass within the chamber 12 increases.

The treated water continually flows through first outlet 21. The culture reduces the phosphate level within the water. The second membrane 22 prevents biomass from being removed through the first outlet 21. The growth rate of the algae is determined, and the second outlet 24 is selectively used to remove a proportion of the biomass produced within the chamber 12 when said biomass reaches a predetermined maximum level so as to maintain a continuous or substantially continuous culture of algae within said chamber 12. When the biomass is below the predetermined level the second outlet 24 is in a closed position. When the biomass within the chamber 12 reaches the predetermined level, the second outlet 24 moves to an open position allowing biomass/treated water to flow from the chamber 12.

When the level of biomass within the chamber 12 is suitably decreased the outlet 24 will be closed. For example, 20% of the biomass may be allowed to leave the chamber. The removed biomass and treated water removed through the second outlet 24 then flows to a separator (not shown) which separates or filters the biomass from the treated waste water. The biomass is then introduced into an anaerobic digester. The anaerobic digester comprises at least one bacterial strain for digesting the biomass. The biomass is converted within the anaerobic digester (not shown) to methane gas and carbon dioxide.

Figure 2:
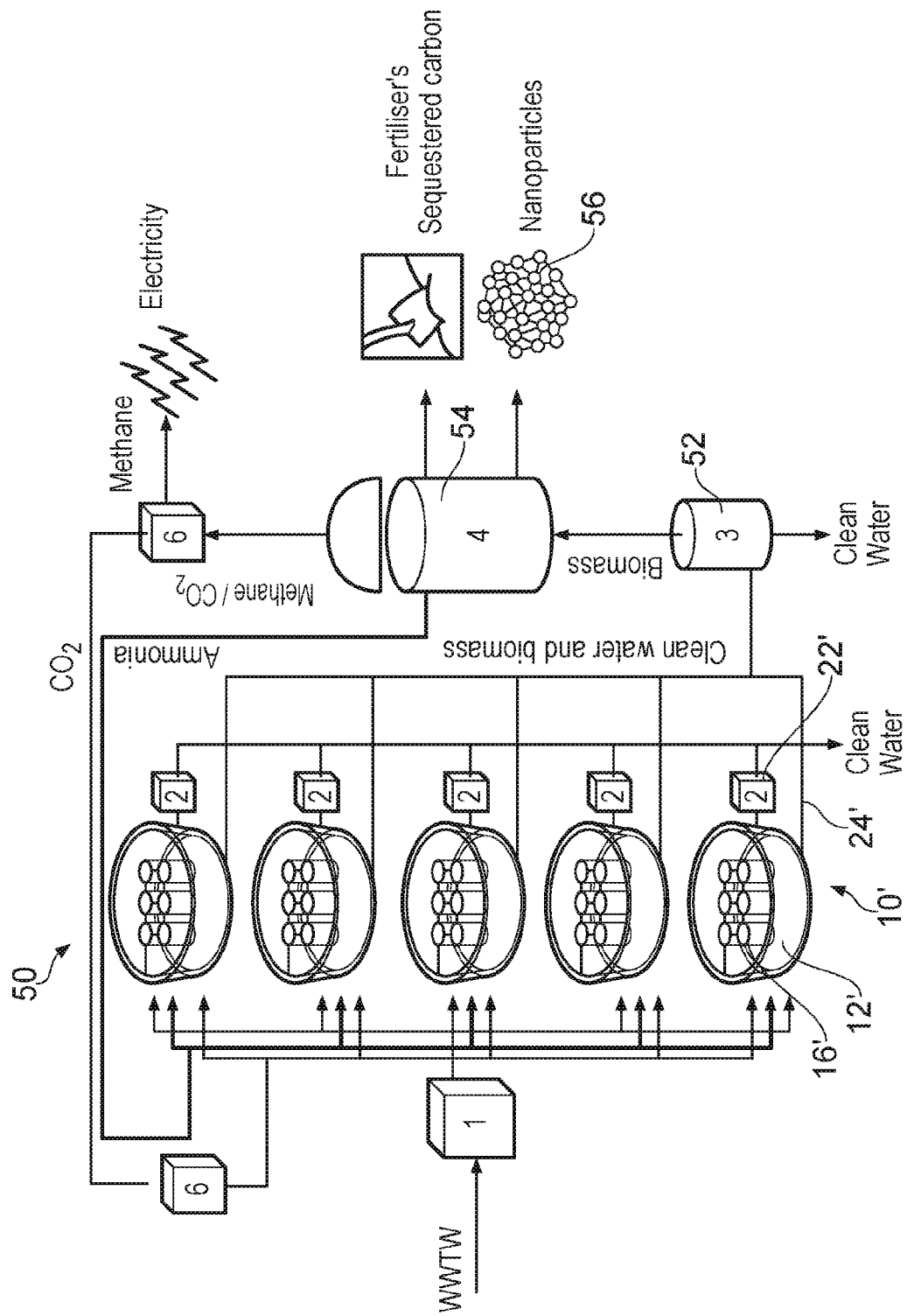
FIG. 2 is a schematic illustration of a waste water treatment system according to one embodiment of the invention.

A waste water treatment system 50 may typically comprise multiple photobioreactors. As shown in FIG. 2, the waste water treatment system 50 may comprise five photobioreactors 10' as shown in FIG. 1. The photobioreactors 10' may each further comprise an inlet (not shown) for supplying metals, such as for example gold and copper to the treatment chamber 12'. The waste water is introduced to the treatment chambers 12'. A slurry of metal is also introduced to the treatment chambers 12'. The LEDs 16' provide a light source to the culture of algae. The culture removes phosphates from the waste water and also ingests the metals to form nanoparticles. The first waste water outlets 22' of the photobioreactors 10' are connected to supply a stream of clean treated water. The second waste water outlets 24' of the photobioreactors 10' are connected to supply a stream of treated water and biomass. The stream provided by the second waste water outlets 24' is supplied to a separator 52. The separator filters the stream so as to supply biomass to the anaerobic digester 54 and clean treated water. In the anaerobic digester 54, the biomass is digested by a bacterial strain. The digestion causes the cell walls to break down and release the nanoparticles of metal 56 for collection. The biomass is converted to methane and carbon dioxide. The methane gas is collected for energy production. The carbon dioxide is recycled into the supply for the photobioreactor. Remaining liquid and solid fragments within the photobioreactor can then be used as liquid and solid fertilisers.

Although the invention has been described above with one or more preferred embodiments, it will be appreciated that various changes and/or modifications may be made without departing from the scope of the invention as defined in the appended claims.

The invention claimed is:

1. A photobioreactor for treatment of waste water comprising:
a treatment chamber having a base and one or more chamber walls extending from the base, and a longitudinal axis, the treatment chamber arranged for receiving a culture of algae having a biomass;
a water inlet arranged for supply of waste water to said treatment chamber;
at least one light source provided within said treatment chamber in the form of an elongate column arranged to extend substantially parallel to the longitudinal axis of the chamber, and operable to provide light to said culture of algae contained within the treatment chamber to promote growth of said culture of said algae, thereby producing an increase in said biomass of said culture of said algae in which the light source comprises at least one flashing light emitting diode (LED) configured for emitting light at an intensity above a pre-determined threshold intensity for damaging the culture of algae without being emitted long enough to cause damage to the culture;
a gas diffuser located across the base of the treatment chamber to provide a diffused air stream into the treatment chamber; and
a first water outlet for removal of treated water;
a second outlet arranged for selective removal of a proportion of the biomass of the culture of algae produced within said chamber when said biomass reaches a predetermined maximum level so as to maintain the biomass of the culture of algae within a predetermined maximum level within said treatment chamber, and
at least one membrane located within the chamber, wherein the at least one membrane has a periphery and the entire periphery of the membrane is in contact with the one or more chamber walls, and wherein the at least one membrane is arranged between the first and second outlets so as to retain said culture of algae within the chamber while allowing treated water to be removed by said first water outlet.

2. The photobioreactor as claimed in claim 1, in which the at least one flashing LED is a high frequency flashing light (FLE), and in which the flashing light is arranged in use to flash so that the ratio of the period of time in which light is emitted to the period of time in which light is not emitted is approximately 1:2.

3. The photobioreactor as claimed in claim 1, in which the light intensity provided by the at least one light source is variable.

4. The photobioreactor as claimed in claim 1, in which the light intensity provided by the at least one light source is variable, and in which the at least one light source is arranged in use to provide an increasing light intensity over a predetermined period of time.

5. The photobioreactor as claimed in claim 1, in which the photobioreactor further comprises an insulating layer.

6. The photobioreactor as claimed in claim 1, in which the wavelengths of light emitted from the at least one light source are calibrated to enhance photosynthesis.

7. The photobioreactor as claimed in claim 1, in which the wavelengths of light emitted from the at least one light source are calibrated to enhance photosynthesis, and in which the at least one light source is calibrated to provide light having predominantly a wavelength in the region of 620 to 645 nm.

8. The photobioreactor as claimed in claim 1, in which the photobioreactor further comprises at least one further membrane located adjacent to or at the water inlet and arranged in use to maintain the sterility of the culture of algae.

9. A photobioreactor for treatment of waste water comprising:
a treatment chamber having a base, one or more chamber walls extending from the base, and a longitudinal axis, the treatment chamber arranged for receiving a culture of algae having a biomass;
a water inlet arranged for supply of waste water to said treatment chamber;
at least one light source provided within said treatment chamber in the form of an elongate column arranged to extend substantially parallel to the longitudinal axis of the chamber, and operable to provide light to said culture of algae contained within the treatment chamber to promote growth of said culture of said algae, thereby producing an increase in said biomass of said culture of said algae in which the light source comprises at least one flashing light emitting diode (LED) configured for the emission of light at an intensity above a pre-determined threshold intensity for damaging the culture of algae without being emitted long enough to cause damage to the culture, and wherein the light intensity of the at least one light source is adjustable in dependence upon the density of the culture of algae received within the treatment chamber;
a gas diffuser located across the base of the treatment chamber to provide a diffused air stream into the treatment chamber; and
a first water outlet for removal of treated water;
a second outlet arranged for selective removal of a proportion of the biomass of the culture of algae produced within said chamber when said biomass reaches a predetermined maximum level so as to maintain the biomass of the culture of algae within a predetermined maximum level within said treatment chamber, and
at least one membrane located within the chamber wherein the at least one membrane has a periphery and the entire periphery of the membrane is in contact with the one or more chamber walls, and the at least one membrane is arranged between the first and second outlets so as to retain said culture of algae within the chamber while allowing treated water to be removed by said first water outlet.

10. The photobioreactor of claim 9 where the adjustable light source is increased in intensity as the culture of algae density increases.

* * * * *